United States Patent [19]

Schach et al.

[11] Patent Number: 5,451,703
[45] Date of Patent: Sep. 19, 1995

[54] PROCESS FOR THE PREPARATION OF BIARYLS

[75] Inventors: Thomas Schach, Hofheim am Taunus; Theodor Papenfuhs, Frankfurt am Main; Joachim Hackenbruch, Mainz, all of Germany

[73] Assignee: Hoechst Aktiengesellschaft, Frankfurt, Germany

[21] Appl. No.: 255,550

[22] Filed: May 31, 1994

Related U.S. Application Data

[63] Continuation of Ser. No. 39,448, Apr. 22, 1993, abandoned.

[30] Foreign Application Priority Data

Oct. 26, 1990 [DE] Germany ............ 40 34 109.7

[51] Int. Cl.⁶ .................................. C07C 1/32
[52] U.S. Cl. ........................ 585/469; 585/425
[58] Field of Search .................... 585/469, 425

[56] References Cited

U.S. PATENT DOCUMENTS 4,727,185  2/1988  Shoji et al. ............. 562/481

FOREIGN PATENT DOCUMENTS 0206543  12/1986  European Pat. Off. .
0318634   6/1989  European Pat. Off. .

Primary Examiner—P. Achutamurthy
Attorney, Agent, or Firm—Connolly and Hutz

[57] ABSTRACT

Process for the preparation of biaryls of the formula (1)

$$R^1{}_m\text{—Ar—Ar—}R^1{}_m \quad (1)$$

wherein Ar is a phenylene or naphthylene radical, $R^1$ is a hydrogen, fluorine or chlorine atom or an unbranched or branched alkyl($C_1$-$C_6$)—, alkyl($C_1$-$C_6$)—O—, alkyl($C_1$-$C_6$)—CO— or alkyl($C_1$-$C_6$)—$SO_2$— radical and m is the number of still unsubstituted $$\underset{=\text{C}-}{\overset{\text{H}}{}}$$

positions on the Ar radical, in which a compound of the formula (2)

$$R^1{}_m\text{—Ar—X} \quad (2)$$

wherein Ar, $R^1$ and m have the meanings cited above and X is a chlorine or bromine atom, is dehalogenated and dimerized in the presence of a palladium catalyst on a support material, of a reducing agent, a hydrogen halide acceptor, a polyether or polyether mixture and of water at temperatures of about 50° to about 120° C.

18 Claims, No Drawings

PROCESS FOR THE PREPARATION OF BIARYLS

This is continuation of Ser. No. 08/039,448, filed Apr. 22, 1993, now abandoned.

The present invention relates to an improved process for the preparation of biaryls by dehalogenation and dimerization of aryl halides in the presence of a palladium catalyst on a support material, of a reducing agent, a hydrogen halide acceptor, a polyether or polyether mixture and of water.

Biaryls have great importance as building blocks for synthesis of pharmaceutical products, but are also required in the fields of plant protection and liquid crystal technology, where fluorinated biaryls are particularly important. The targeted introduction of a fluorine substituent into a biaryl structure is in many cases only possible by a laborious and thus expensive Balz-Schiemann reaction. The limits of this reaction lie on the one hand in the availability of the starting compounds and on the other in the high toxicity of some of them (e.g. benzidine), both being arguments that greatly restrict its potential for synthesis.

For the synthesis of the desired biaryls by synthetic reactions from already fluorinated compounds a number of coupling reactions are available. These either require extensive technical effort (electroreductive coupling, Grignard reactions) or give the desired biaryls in only moderate yields (Ullmann coupling) or with poor selectivity (Gomberg-Bachmann reaction).

A further possibility for the preparation of biaryls is given by a dehalogenation-dimerization reaction in the presence of noble metal catalysts, a reducing agent and a hydrogen halide acceptor (M. Busch and W. Weber; Journal f. prakt. Chemie, 146, 1–55, 1936; F. R. Mayo and M. D. Hurwitz, J. Chem. Soc., 71, 776–779, 1949; P. Bamfield and P. M. Quan, Synthesis 7, 537–538, 1978). The problem with this type of reaction lies in the frequently unfavorable selectivity with which the desired biaryl is obtained. Thus as well as the desired biaryls the dehalogenated starting compounds always occur, which thereby reduces, sometimes significantly, the yields. A further disadvantage lies in the rapid reduction in selectivity of the catalyst during repeated use, thereby setting firm limits on the technical application of this reaction (see e.g.: F. R. Mayo and M. D. Hurwitz, J. Chem. Soc., 71, 776–779, 1949).

This synthesis method was used with various reducing agents for the preparation of biaryls (EP 206 543), in particular for the synthesis of 3,3′,4,4′-diphenyltetracarboxylic acid (U.S. Pat. No. 4,727,185, EP 318 634). The hitherto known reactions of this type give at most only moderate yields of the desired biaryls.

It has now surprisingly been found that biaryls of the formula (1)

$$R^1{}_m\text{—Ar—Ar—}R^1{}_m \qquad (1)$$

in which Ar is a phenylene or naphthylene radical, $R^1$ is a hydrogen, fluorine or chlorine atom or an unbranched or branched alkyl($C_1$-$C_6$)—, alkyl($C_1$-$C_6$)—O—, alkyl($C_1$-$C_6$)—CO— or alkyl($C_1$-$C_6$)—SO$_2$— radical and m is the number of still unsubstituted

positions on the Ar radical, can be prepared advantageously in good yields and with high selectivity, by dehalogenating and dimerizing a compound of the formula (2)

$$R^1{}_m\text{—Ar—X}$$

in which Ar, $R^1$ and m have the meanings cited above and X is a chlorine or bromine atom, in the presence of a palladium catalyst on a support material, of a reducing agent, a hydrogen halide acceptor, a polyether or polyether mixture and of water at temperatures from about 50° to about 120° C., preferably from about 70° to about 110° C.

In particular it was found that the dehalogenating dimerization in the presence of a polyether or polyether mixture has a decisive influence on the selectivity of the coupling reaction with the consequence of a significant increase in yield.

Possible examples of polyether or polyether mixtures are those of the formula (3)

$$R^3\text{—(O—CH}_2\text{—CH}_2\text{—)}_p\text{OR}^4 \qquad (3)$$

in which $R^3$ and $R^4$ are the same or different linear or branched alkyl($C_1$-$C_6$)— radicals, such as methyl, ethyl, propyl, butyl, pentyl, hexyl, i-propyl or i-butyl groups, and p is a number from 1 to about 20.

The polyether or polyether mixture is used in amounts from about 0.1 to about 500% by weight, preferably from about 1 to about 100% by weight, related to the aryl halide used.

Through the presence of polyethers or polyether mixtures in the dehalogenating dimerization, a marked increase in selectivity as well as an increase in catalyst activity can be established, with the consequence that in particular during recycling of catalyst already used in the process according to the invention, scarcely any losses in selectivity can be established, which is in marked contrast to the solvent-free reaction variant.

The hydrogen halide acceptor can expediently be an inorganic compound of an alkali metal or alkaline earth metal, for example the hydroxide, carbonate or hydrogen carbonate of lithium, sodium, potassium, rubidium, cesium, magnesium, calcium, barium or strontium or mixtures thereof. Preferably, sodium compounds, in particular sodium hydroxide, are used. However, for example, sodium methylate can also be used as acceptor.

It is expedient to use the hydrogen halide acceptor in the form of an aqueous solution, containing about 50 to about 500 mol %, preferably about 100 to about 350 mol %, more preferably about 150 to about 200 mol %, per mole of aryl halide used. The concentration of the aqueous alkali metal or alkaline earth metal compound exerts a decisive influence on the selectivity of the coupling reaction, where it is expedient to use concentrations from about 5 to about 50% by weight, preferably from about 15 to about 40% by weight.

The palladium catalyst possible according to the invention is used in the form of metallic palladium on a support material. Possible support materials are for example activated charcoal, potassium carbonate, barium carbonate, silicon, aluminum, titanium oxide or magnesium. Palladium on activated charcoal has proven to be the most favorable catalyst form.

The content of metallic palladium lies in the range from about 0.1 to about 20% by weight, related to the support material; catalysts with about 1 to about 10% by weight are preferred, preferably 5% by weight.

It was established that the amount of catalyst used has a decisive influence on the selectivity of the reaction. Excessive catalyst amounts lead to unwanted side reactions, whereas insufficient amounts of the palladium catalyst lead to premature termination of the reaction, or very long reaction times and an increased proportion of uncoupled reduced aromatic starting compounds must be reckoned with. In general the catalyst is used in amounts from about 0.001 to about 50 mmol, preferably from about 0.5 to about 2 mmol of palladium, per mole of aryl halide used.

For repeated application, the catalyst can be used again untreated, or pretreated with alcohols (e.g. methanol, ethanol), polyethers, ethers, or water or steam.

The reducing agent in the present invention can be for example alcohols, formaldehyde, formates or hydrazine. Individual examples for this are methanol, glycerol, ethylene glycol, formalin, paraformaldehyde and sodium formate. Polyhydric alcohols such as ethylene glycol or glycerol are preferably used. The reducing agent as a rule is used in an amount from about 0.1 to about 20 mol, preferably from about 0.1 to about 1 mol per mole of aryl halide used.

In general the reaction medium is a three phase system of organic and aqueous phase as well as the heterogeneous palladium catalyst, for which reason good stirring is of great importance.

With regard to the temperature ranges given previously for the process according to the invention, it can additionally be noted that at temperatures over 120° C. working under pressure is required. When working below 50° C. the reaction becomes very slow; in addition it no longer runs to completion.

In the preferred temperature range the reaction times lie between 0.5 and 100 hours, depending on the aryl halide used, the catalyst concentration, the amount of base, the base concentration, the proportion of polyethers and the amount and type of reducing agent used. The reaction initially proceeds very rapidly, so that even after 2 hours conversions of 50 to 70 mol % are achieved. In order to reach conversions over 95 mol %, long reaction times may be required, so that early termination of the reaction (80–95 mol % conversion) is convenient.

The reaction of the present invention can be carried out under a protective gas, for example argon or nitrogen. It is preferred to work in the presence of atmospheric oxygen.

The aryl halide used can be liquid or solid. At the reaction temperature, however, it should be completely liquid or completely in solution.

In principle different aryl halides can be simultaneously used for the reaction according to the invention. Biaryl mixtures are thereby formed, which can however be difficult to separate. The process according to the invention can also be applied to other isocyclic chlorinated or brominated aromatic compounds as well as to heterocyclic chlorinated or brominated aromatic compounds.

The process described here for the preparation of biaryls leads to markedly higher selectivities and yields than is the case with comparable known reactions. Thus, for example, in Synthesis 7, 537–538, 1978 (P. Bamfield and P. M. Quan), the dimerization of 2-bromotoluene is described, which furnishes 2,2'-bitolyl in yields of only 33%. EP 206 543 describes the analogous reaction with 2-chlorotoluene and with 2-bromotoluene with yields of 60 and 55 mol %. The comparable dimerization reaction of 2-bromo-5-fluorotoluene according to the process described here furnishes markedly better yields. The analogous is also true for the dimerization of chlorobenzene and bromobenzene, the yields of which of 48% and 30–65% (Synthesis 7) are markedly surpassed by the process described here and the corresponding fluorinated starting compounds.

The following examples serve to illustrate more closely the process according to the invention, without restricting it thereto.

EXAMPLE 1

In a 1 liter three neck flask with stirrer, internal thermometer and reflux condenser are placed 457.1 g of 35% sodium hydroxide solution, 350.0 g of 4-bromofluorobenzene (BrFB), 175.0 g of diethylene glycol dimethyl ether, 20.0 g of polyethylene glycol dimethyl ether 500 and 5.8 g of Pd/C (5%, 50% moisture). The reaction suspension is heated to 100° C. and during the course of 2 hours 62.1 g of ethylene glycol are added. For a further 16 hours the reaction suspension remains at this temperature. The catalyst is then removed and the organic phase fractionally distilled. For GC analyses of the reaction solution and the yields of isolated 4,4'-difluorobiphenyl see Table 1 which follows.
Melting range: 89.1°–91.0° C.
Solidification point: 88.9° C.

EXAMPLE 2

Starting set-up and reaction course analogous to Example 1, with the recycled catalyst from Example 1. For GC analyses of the reaction solution and the yields of isolated 4,4'-difluorobiphenyl see Table 1 which follows.

EXAMPLE 3

Starting set-up and reaction course analogous to Example 1, with the recycled catalyst from Example 2. For GC analyses of the reaction solution and the yields of isolated 4,4'-difluorobiphenyl see Table 1 which follows.

EXAMPLE 4

In a 1 liter three neck flask with stirrer, internal thermometer and reflux condenser are placed 160.0 g of sodium hydroxide pellets dissolved in 800.0 g of H$_2$O together with 260 g of 4-chlorofluorobenzene (ClFB), 90.0 g of diethylene glycol dimethyl ether, 20.0 g of polyethylene glycol dimethyl ether 500 and 8.0 g of Pd/C (5%, 50% moisture) in the reaction vessel. The reaction suspension is heated to 100° C. and during the course of 4 hours 84.8 g of 87% glycerol are added. For a further 16 hours the reaction suspension remains at this temperature. The catalyst is then removed and the organic phase fractionally distilled. For GC analyses of the reaction solution and the yields of isolated 4,4'-difluorobiphenyl see Table 1 which follows.

EXAMPLE 5

Test carried out analogously to Example 1 with the following reaction components: 114 g of 35% sodium hydroxide solution, 94.5 g of 2-bromo-5-fluorotoluene (BrFT), 40.0 g of diethylene glycol dimethyl ether, 5 g of polyethylene glycol dimethyl ether 500, 2.5 g of Pd/C (5%, 50% moisture) and 21.5 g of 87% glycerol.

For GC analyses of the reaction solution and the yields of isolated 4,4'-difluoro-2,2'-bitolyl see Table 1 which follows.

Solidification point: 22.4° C.

EXAMPLE 6

Test carried out analogously to Example 1 with the following reaction components: 114 g of 35% sodium hydroxide solution, 96.5 g of 2,4-difluorobromobenzene (DFBrB), 40.0 g of diethylene glycol dimethyl ether, 5 g of polyethylene glycol dimethyl ether 500, 2.0 g of Pd/C (5%, 50% moisture) and 21.5 g of 87% glycerol. The catalyst is removed, the organic phase is freed from solvent and the crude product obtained is recrystallized from chlorobenzene. For GC analyses of the reaction solution and the yields of isolated 2,2',4,4'-tetrafluorobiphenyl see Table 1 which follows.

Melting range: 141.5°–145.5° C.
Solidification point: 138.1° C.

COMPARISON EXAMPLE 1

Starting set-up and test procedure analogously to Example 1 without addition of diethylene glycol dimethyl ether and polyethylene glycol dimethyl ether 500. For GC analyses of the reaction solution see Table 1 which follows.

COMPARISON EXAMPLE 2

Starting set-up and test procedure analogously to Example 2 without addition of diethylene glycol dimethyl ether and polyethylene glycol dimethyl ether 500. For GC analyses of the reaction solution see Table 1 which follows.

COMPARISON EXAMPLE 3

Starting set-up and test procedure analogously to Example 3 without addition of diethylene glycol dimethyl ether and polyethylene glycol dimethyl ether 500. For GC analyses of the reaction solution see Table 1 which follows.

COMPARISON EXAMPLE 4

Starting set-up and test procedure analogously to Example 5 without addition of diethylene glycol dimethyl ether and polyethylene glycol dimethyl ether 500. For GC analyses of the reaction solution see Table 1 which follows.

TABLE 1

| Ex. | Time (h) | Temp. (°C.) | Conversion | Yield by GC mole (%) H—Ar | Ar—Ar | Ar—Ar* | Yields iso. mol (%) Ar—Ar* | Ar—X |
|---|---|---|---|---|---|---|---|---|
| 1 | 18 | 100 | 100.0 | 10.3 | 89.1 | 89.1 | 87.8 | BrFB |
| 2 | 18 | 100 | 88.7 | 10.8 | 76.4 | 86.3 | 84.8 | BrFB |
| 3 | 20 | 100 | 87.0 | 13.2 | 73.6 | 84.2 | 82.0 | BrFB |
| 4 | 20 | 95 | 87.5 | 20.7 | 66.0 | 75.5 | 73.2 | ClFB |
| 5 | 20 | 100 | 90.7 | 16.6 | 72.8 | 80.4 | 79.5 | BrFT |
| 6 | 18 | 100 | 100 | 11.8 | 87.1 | 87.1 | 76.3 | DFBrB |
| C1 | 18 | 100 | 100.0 | 14.1 | 82.7 | 82.7 | | BrFB |
| C2 | 18 | 100 | 100.0 | 24.4 | 72.8 | 72.8 | | BrFB |
| C3 | 18 | 100 | 98.2 | 27.6 | 68.9 | 70.2 | | BrFB |
| C4 | 20 | 100 | 100.0 | 31.0 | 65.7 | 65.7 | | BrFT |

*Yields relative to converted aryl halide
In the last column B = benzene and T = toluene.

We claim:

1. A process for the preparation of biaryls of the formula (1)

$$R^1{}_m-Ar-Ar-R^1{}_m \quad (1)$$

in which Ar is a phenylene or naphthylene radical, $R^1$ is a fluorine or chlorine atom or an unbranched or branched alkyl ($C_1$-$C_6$)—, alkyl($C_1$-$C_6$)—O—, alkyl(-$C_1$-$C_6$)—CO— or alkyl ($C_1$-$C_6$)—$SO_2$—radical and m is the number of $R^1$ substituents, on the Ar radical, comprising the step of:

dehalogenating and dimerizing a compound of the formula (2)

$$R^1{}_m-Ar-X \quad (2)$$

in which Ar, $R^1$ and m have the meanings cited above and X is a chlorine or bromine atom, in the presence of a reaction medium containing:
a palladium catalyst on a support material,
a reducing agent,
a hydrogen halide acceptor,
at least one polyether, and water,
at temperatures from about 50° to about 120° C., wherein the reaction medium contains an organic phase, an aqueous phase, and a heterogeneous catalyst phase, and wherein the polyether is of the formula (3)

$$R^3-(OCH_2-CH_2-)_pOR^4 \quad (3)$$

in which
$R^3$ and $R^4$ are linear or branched alkyl ($C_1$-$C_6$)—radicals, and
p is a number from 1 to about 20.

2. The process as claimed in claim 1, wherein in the case m=1, $R^1$ is a fluorine atom.

3. The process as claimed in claim 1, wherein in the case m=2, $R^1$ is a fluorine atom.

4. The process as claimed in claim 1, wherein in the case m=2, on the same Ar radical one $R^1$ is a fluorine atom and the other $R^1$ is a methyl group.

5. The process as claimed in claim 1, wherein the polyether comprises a mixture of polyethers of the formula 3.

6. The process as claimed in claim 1, wherein a polyether or a mixture of polyethers is used at about 0.1 to about 500% by weight, relative to the aryl halide used.

7. The process as claimed in claim 1, wherein a polyether or a mixture of polyethers is used at about 1 to about 100% by weight, relative to the aryl halide used.

8. The process as claimed in claim 1, wherein an inorganic alkali metal or alkaline earth metal compound or sodium methylate is used as hydrogen halide acceptor.

9. The process as claimed in claim 1, wherein the hydrogen halide acceptor is used in an amount of about 0.5 to about 50 mol, per mole of aryl halide used.

10. The process as claimed in claim 1, wherein the hydrogen halide acceptor is an about 5 to 50 percent by weight aqueous solution.

11. The process as claimed in claim 1, wherein the hydrogen halide acceptor is an about 15 to 40 percent by weight aqueous solution.

12. The process as claimed in claim 1, wherein the palladium catalyst on a support material is a palladium catalyst on activated charcoal or calcium carbonate.

13. The process as claimed in claim 1, wherein said catalyst contains about 0.1 to about 20% by weight of metallic palladium, relative to the support material.

14. The process as claimed in claim 1, wherein palladium is used at about 0.001 to about 50 mmol, per mole of the aryl halide used.

15. The process as claimed in claim 1, wherein the palladium catalyst on a support material is a palladium catalyst on support material which has previously been used repeatedly in the dehalogenation and dimerization.

16. The process as claimed in claim 1, wherein the reducing agent is monohydric or polyhydric alcohol, formaldehyde, a formate, or hydrazine.

17. The process as claimed in claim 1, wherein the reducing agent is methanol, glycerol, ethylene glycol, formalin, paraformaldehyde or sodium formate.

18. The process as claimed in claim 1, wherein the reducing agent is used in an amount of about 0.1 to about 200 mol %, per mole of aryl halide used.

* * * * *